United States Patent [19]

Yuan et al.

[11] Patent Number: 4,892,517

[45] Date of Patent: Jan. 9, 1990

[54] BREAST PUMP

[75] Inventors: Arthur H. Yuan, Hudson, Ohio; Michael S. Joss, Chicago, Ill.

[73] Assignee: Spalding & Evenflo Companies, Inc., Tampa, Fla.

[21] Appl. No.: 179,822

[22] Filed: Apr. 11, 1988

[51] Int. Cl.⁴ .............................................. A61M 1/06
[52] U.S. Cl. ......................................................... 604/74
[58] Field of Search ..................................... 604/73-75

[56] References Cited

U.S. PATENT DOCUMENTS

| | | | |
|---|---|---|---|
| 108,882 | 11/1870 | Colvin | 604/74 |
| 3,977,405 | 8/1976 | Yanase | 604/74 |
| 4,573,969 | 3/1986 | Schlensog et al. | 604/74 |

FOREIGN PATENT DOCUMENTS

| | | | |
|---|---|---|---|
| 0762701 | 12/1956 | United Kingdom | 604/74 |
| 2082920 | 3/1982 | United Kingdom | 604/75 |

Primary Examiner—Dalton L. Truluck
Assistant Examiner—Denise W. DeFranco
Attorney, Agent, or Firm—Donald R. Bahr

[57] ABSTRACT

An improved breast pump comprised of a manifold having a cavity and plurality of openings. A horn is positioned in one of the openings for coupling the mother's breast with the cavity. A first fixed cylinder is formed integrally with a second opening of the manifold with a second cylinder slidingly received over the first cylinder for effecting a pumping action therebetween to create a reduced pressure within the horn, cavity and cylinders. A third opening is for the coupling of a baby bottle therewith. A ball valve is located within the third opening whereby when the second cylinder is reciprocated with respect to the first cylinder and a vacuum created in the horn, cavity and cylinders, the ball valve will seal the third opening and the bottle from the cavity and suck milk from a mother's breast located in association with the horn.

6 Claims, 3 Drawing Sheets

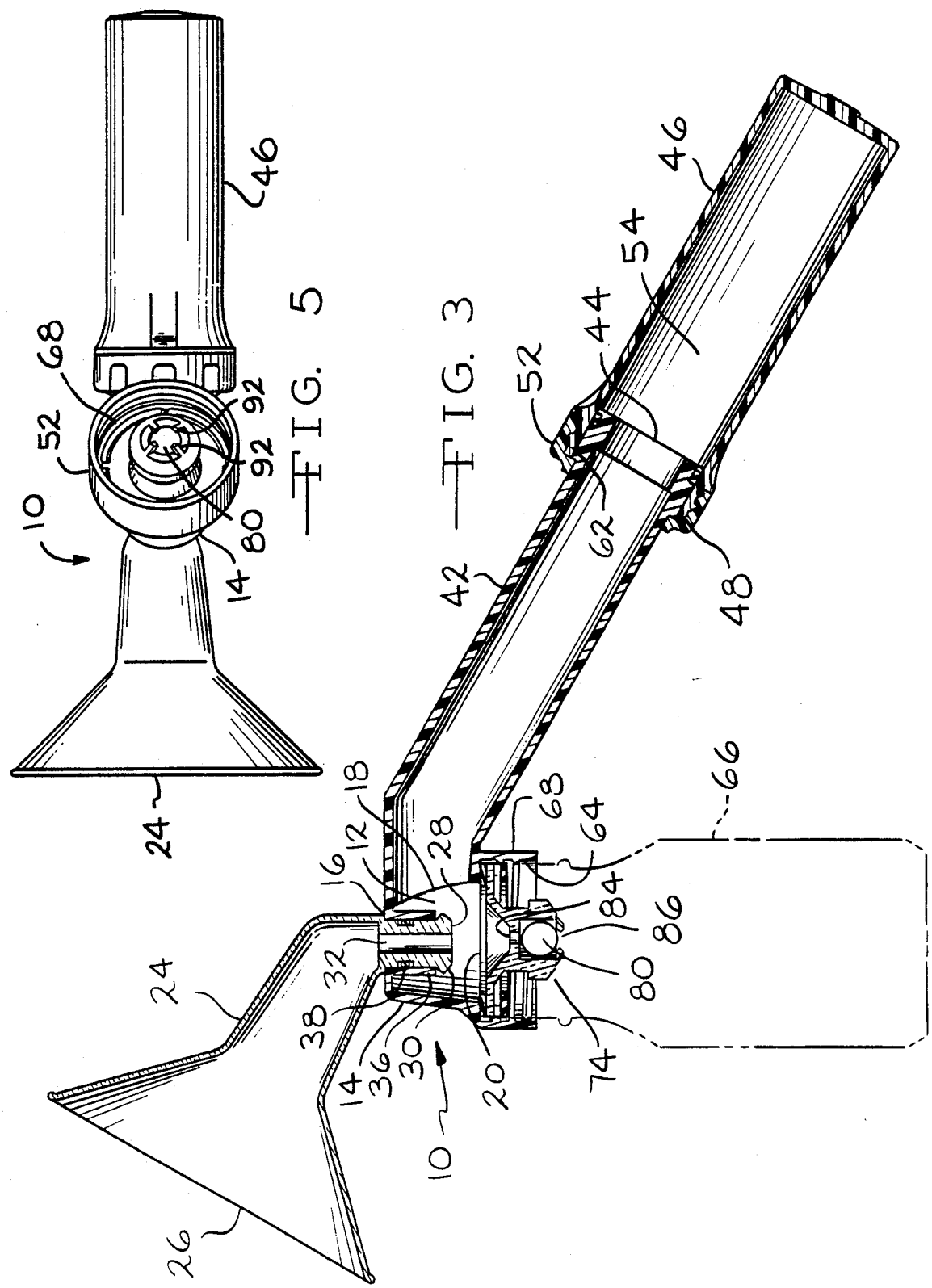

BREAST PUMP

BACKGROUND OF THE INVENTION

1. Field of the Invention

This invention relates to pumps and, more particularly, to manually operated pumps designed to extract milk from the breast of a mother.

2. Description of the Background Art

It has long been known that breast feeding is the most desirable form of nourishment for infants. It is also well known that prepared formulas, while acceptable, are inadequate substitutes for a mother's natural milk.

In recent years there has been a trend for mothers to feed their infants other than from the breast and other than nature's own unadulterated milk. Breast feeding may in some instances be difficult or inconvenient thereby rendering the feeding of prepared formula easier. In some instances, however, a mother will extract milk from her own breast and store it for feeding to the infant at a different time and place. Such a situation may occur when a mother is separated from her child for one reason or another as, for example, when the mother is ill, at work or in a public place whereat the exposing of a breast for feeding purposes would be considered inappropriate. With these considerations in mind, it is apparent that a need exists for a breast pump by which the mother may conveniently extract her own milk at a time and place of her own choice for feeding to her infant at a time and place of her infant's choice.

A wide variety of devices have been developed for use in extracting milk from the mother's breast. One type of device is disclosed in U.S. Pat. No. 3,977,405 to Yanase and in U.S. Pat. No. 4,573,969 to Schlensog. According to those disclosures, the flared end or horn of a first tube is placed in contact with the mother's breast to be pumped. A second or external tube is positioned over the end of the first tube on the side remote from the flared end. A reciprocating or pumping action by the mother of the second tube with respect to the first will apply suction for the withdrawing of the milk. The milk is then received at the bottom of the second tube. A device of this type requires the pouring of the collected milk into a container such as a baby bottle for subsequent feeding to the infant. Designs of this type are quite simple but, unfortunately, result in the seals for the mating parts being contacted by the milk which wear and require replacement. Such designs also complicate the sterilizing of the apparatus between uses.

Further types of devices for milking mothers' breasts are described in U.S. Pat. No. 4,263,912 to Adams and U.S. Pat. No. 4,583,970 to Kirchner. According to those disclosures, a baby bottle is coupled directly with the horn contacting the mother's breast. Vacuum-creating mechanisms of the squeeze-ball type or the pivoting-handle type are coupled with the bottle and horn. A plurality of valves, at least two, are required to effect the suction needed for milk extraction. The plurality of parts required, including the multiplicity of valves, increases the cost of such devices. In addition, the plurality of valves increases the number of moving parts which might malfunction and create problems of operability. Further, although a feeding bottle is coupled directly to the apparatus in order to preclude the step of transferring the milk from the pump to the bottle, the space within the bottle is directly coupled with, and part of, the vacuum space thereby increasing the volume wherein the suction must be produced. Such an arrangement decreases the efficiency of the pumping action thereby requiring excess work by the mother during the extracting of her milk.

An additional type of apparatus for milk extraction is disclosed in U.S. Pat. No. 4,311,141 to Diamond. According to that disclosure, a horn positionable in contact with the breast to be milked, is coupled to the bottle through an arrangement of a hand pump, flexible tube and plurality of valves. The valve at the opening of the bottle removes the fixed volume of the bottle from the variable volume of the chamber wherein vacuum is created. As such its efficiency is improved. The apparatus, however, still has an excessive number of parts and a plurality of valves which inherently increases the cost, complexity and possibility of an operational malfunction. Further, the use of the flexible tubing makes the task of sterilizing the apparatus between uses all the more difficult.

As illustrated by the great number of prior background disclosures and commercial devices, efforts are continuously being made in an attempt to more efficiently extract milk from the breasts of mothers. None of these prior efforts, however, suggests the present inventive combination of component elements arranged and configured for extracting milk more conveniently and efficiently and for rendering such device more economical and convenient to manufacture and clean. Prior devices do not provide the benefits of the present invention which achieves its intended purposes, objectives and advantages over the devices of the background disclosures through a new, useful and unobvious combination of component elements, through a decrease in the number of functioning parts, at a reduction in cost to manufacture and maintain and through the utilization of only readily available materials and conventional components.

It is, therefore, it is an object of the present invention to provide pumping apparatus comprising a central manifold with a cavity having a plurality of openings; a horn positioned in association with one of the openings for coupling a mother's breast with the cavity; a pump positioned in association with a second of the openings to create a vacuum within the cavity; support means positioned in association with a third of the openings for retaining a baby bottle in position to receive pumped milk; and valve means located within the third opening whereby when the pump is activated and a vacuum is created in the cavity, the valve means will seal the third opening from the vacuum in the cavity.

It is a further object of the present invention to reduce the number of parts in devices fro extracting milk from mothers' breasts for simplicity of assembly, disassembly and cleaning.

It is yet a further object of the invention to render hand pumps for extraction of mother's milk more convenient by the adjustablity of the position of the components thereof so that the angle between that portion contacting the mother's breast and the rest of the device may be varied to the particular needs of any particular mother.

Lastly, it is an object of the invention to increase the efficiency of pumps by separating the space of the milk-receiving bottle from the space where the vacuum is created.

The foregoing has outlined some of the more pertinent objects of the invention. These objects should be construed to be merely illustrative of some of the more prominent features and applications, of the intended invention. Many other beneficial results may be attained by applying the disclosed invention in a different manner or by modifying the invention within the scope of the disclosure. Accordingly, other objects and advantages as well as a fuller understanding of the invention may be had by referring to the summary and detailed description of the preferred embodiment of the invention in addition to the scope of the invention as defined by the claims taken in conjunction with the accompanying drawings.

SUMMARY OF THE INVENTION

The invention is defined by the appended claims with the specific preferred embodiment shown in the attached drawings. For the purposes of summarizing the invention, the invention may be incorporated into pumping apparatus comprising a manifold with a cavity and a plurality of openings; a horn positioned in association with one of the openings for coupling a mother's breast with the cavity; a pump positioned in association with a second of the openings to create a vacuum within the cavity; support means positioned in association with a third of the openings for retaining a baby bottle in position to receive pumped milk; and valve means located within the third opening whereby when the pump is activated and a vacuum created in the cavity, the valve means will seal the third opening from the vacuum in the cavity. The horn is rotatable within the manifold. The pump includes a first internal cylinder formed with the manifold and a second external cylinder slidingly received over the first cylinder. The valve includes a housing and a ball located therein, the ball being movable between an upper position by the vacuum within the cavity wherein the third opening is sealed and a lower position wherein the third opening is not sealed.

The invention may also be incorporated into a breast pump for extracting milk from a mother's breast comprising: a central manifold having a cavity having a plurality of openings; a horn rotatably positioned in one of the openings for coupling a mother's breast to be milked with the cavity of the manifold; a first fixed cylinder formed integrally with a second opening of the manifold; a second cylinder reciprocatingly received on the first cylinder for effecting a pumping action therebetween to create reduced pressure in the space within the horn, manifold and cylinders; a third opening within the manifold for the coupling of the baby bottle therewith; and a ball valve located within the third opening whereby, when the second cylinder is reciprocated with respect to the first cylinder and a vacuum created in the space within the horn, manifold and cylinders, the ball valve will seal the third opening and the bottle from the space of reduced pressure and suck milk from a mother's breast in association with the horn. The horn is symmetric about a first axis over the majority of its extent and also includes a projection symmetric about a second axis positionable in the manifold, with the first and second axes of the horn being at an angle with respect to each other. The cylinders are symmetric about an axis extending at an angle from the manifold. The breast pump further includes a cap slidably received on the first cylinder and with internal threads matable with external threads on the inboard end of the second cylinder and an enlargement on the outboard end of the first cylinder to retain the cylinders in sliding relationship with each other. The various components of the breast pump are all separable one from another.

The invention may also be incorporated into an apparatus for extracting milk from a mother's breast comprising a central manifold having a cavity and a plurality of openings; a horn rotatably positioned in one of the openings for coupling a mother's breast to be milked with the cavity of the manifold; a first fixed cylinder formed integrally with a second opening of the manifold; a second cylinder reciprocatingly received on the first cylinder for effecting a pumping action therebetween to create reduced pressure in the space within the horn, manifold and cylinders; a third opening within the manifold; a baby bottle separably coupled with the third opening; and a ball valve located within the third opening whereby when the second cylinder is reciprocated with respect to the first cylinder and a vacuum created in the space within the horn, manifold and cylinders, the ball valve will seal the third opening and the bottle from the space of reduced pressure and suck mild from a mother's breast in association with the horn. The apparatus further includes a stand with a flat lower face and a recess thereabove for receiving and supporting the baby bottle therein.

The foregoing has outlined rather broadly the more pertinent and important features of the present invention in order that the detailed description of the invention that follows may be further understood whereby the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis of modifying or designing other apparatus for carrying out the same purposes of the present invention. It should also be realized by those skilled in the art that such equivalent apparatus does not depart from the spirit and scope of the invention as set forth in the appended claims.

BRIEF DESCRIPTION OF THE DRAWINGS

For a fuller understanding of the nature and objects of the invention, reference should be had to the following detailed description taken in conjunction with the accompanying drawings in which:

FIG. 3 is a sectional view similar to that shown in FIG. 2 but with the cylinders in their expanded orientation;

FIG. 5 is a bottom view of the manifold showing the ball valve in greater detail.

Similar reference numbers refer to similar parts throughout the various figures.

DETAILED DESCRIPTION OF THE INVENTION

Figure 2:
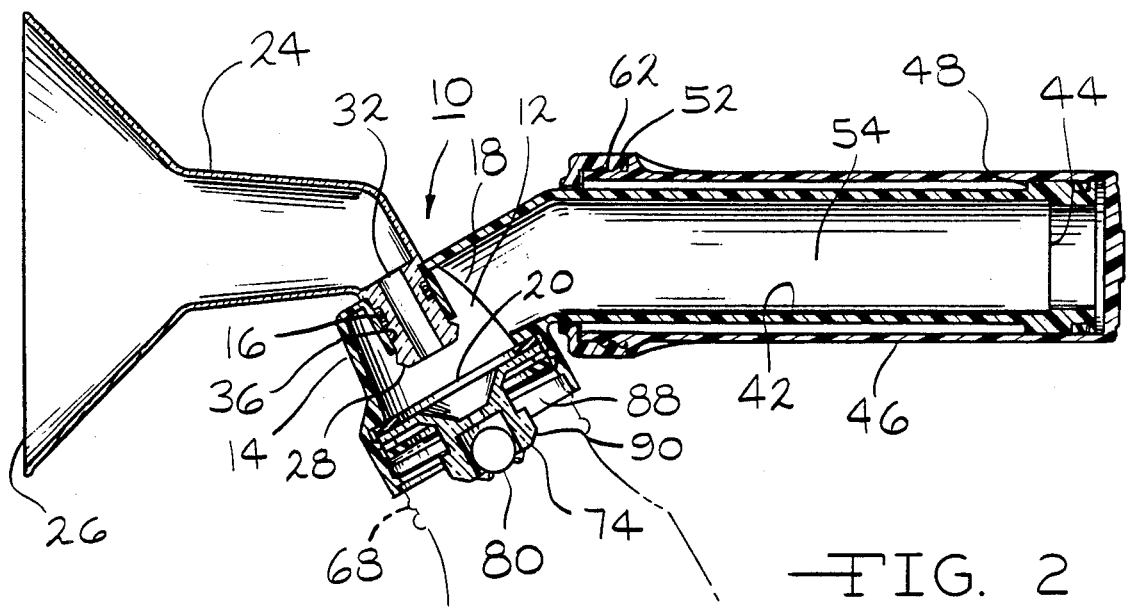
FIG. 2 is a sectional view of the pump shown in FIG. 1 but with the cylinders in their contracted orientation.
Figure 1:
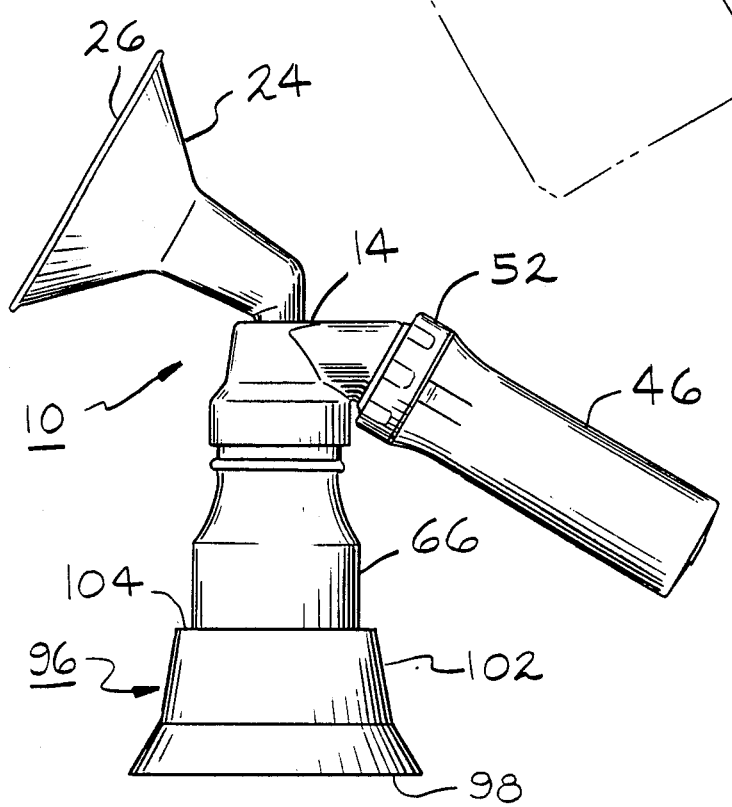
FIG. 1 is a side elevational view of the breast pump constructed in accordance with the present invention shown in combination with a stand for receiving and supporting the breast pump when a bottle is secured thereto.
Figure 4:
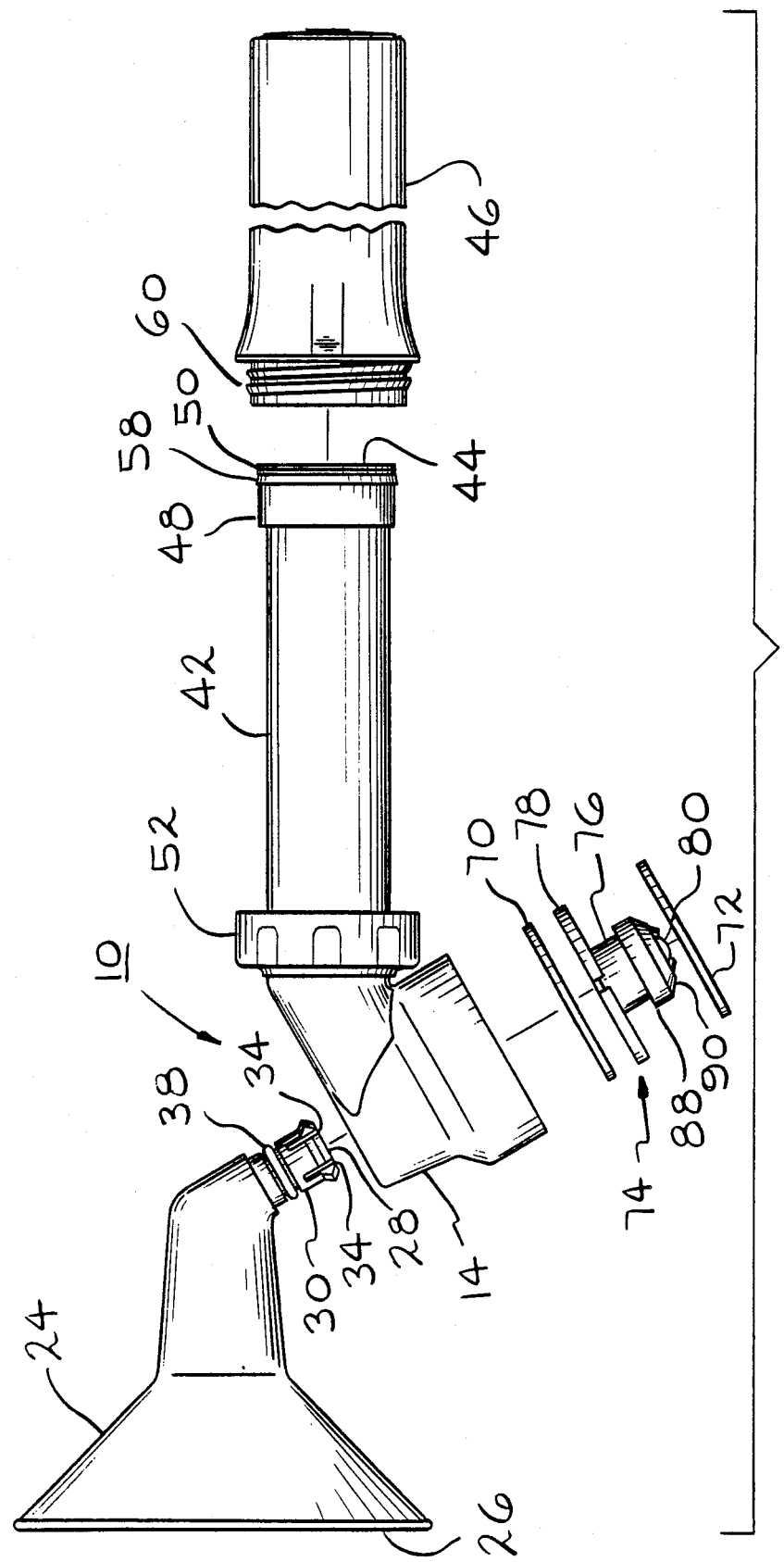
FIG. 4 is an exploded side elevational view showing the various component parts of the breast pump of the previous figures.

Shown in the various figures is an apparatus 10 for the extracting of milk from the breast of a mother. The apparatus functions on the principle of creating a vacuum within a cavity 12 in the apparatus so that the vacuum can suck milk from the mother's breast.

The principle component element of the apparatus is a central manifold 14. The manifold has a cavity 12 communicating with three separate openings 16, 18 and 20. The first opening 16 is adapted to receive a horn 24 formed with an outboard end 26, flared in configuration, for being placed in sealing contact with the mother's to be milked. The opposite or inboard end 28 is formed with a cylindrical projection 30 of an enlarged cross-sectional diameter and a central hole 32 extending therethrough for effecting fluid communication between the cavity and the breast to be pumped. Axial slots 34 in the projection permit expansion and contraction for separating the projection from the manifold. A cylindrical flange 36 is formed as an internal projection of the first opening. The projection has a cylindrical bearing surface of a reduced diameter in contact with the flange for rotation of the projection and horn with respect to the remainder of the apparatus. An O-ring 38 is located in a recess of the projection for pneumatically sealing the first opening.

The major extent of the horn is symmetric about an axis which is at an angle with respect to the axis of the projection 30. This construction allows for varying the angular orientation of the horn with respect to the remainder of the apparatus for greater convenience of the mother in positioning the apparatus with respect to her breast.

The second opening 18 communicating with the cavity is located in association with a first or interior cylinder 42. The first cylinder is preferably formed integrally with the manifold and has an open outboard end 44. The first cylinder has an axis which is angled with respect to the axis of the second opening. This orientation is again for the convenience of the mother in adjusting the apparatus to a proper angle for comfort during use.

A second or exterior cylinder 46 is located axially aligned with the first cylinder whereby its internal surface is in sliding contact with respect to the external surface of the first cylinder at the outboard end. An end enlargement 48 with an external annular groove 50 secured as by an adhesive to the outboard end of the first cylinder to hold a cap 52 in location on the first cylinder. Reciprocation of the second cylinder with respect to the first cylinder will vary the volume of the chamber 54 within the cylinders for creating a pumping action and vacuum within the cylinders, cavity 12 and horn 24. The groove 50 of the outboard end of the internal cylinder is provided with an elastomeric gasket 58 to preclude inadvertent escape of air from within the cylinders for increasing the pumping efficiency of the apparatus.

The inboard end of the second cylinder is provided with external threads 60 which couple with the internal threads 62 of the cap 52 located in sliding relationship over the first cylinder. The cap has an inboard diameter that is smaller than the exterior diameter of the enlargement 48 to preclude separation of the cap from the first cylinder. The enlargement 48 with its gasket 58, however, will permit the second cylinder and cap to be slid with respect to the first cylinder and will allow the unscrewing of the threads 60 and 62 between the cap and the second cylinder for separating the cylinders for cleaning purposes.

The third opening 20 of the manifold is formed with internal threads 64 for the receipt of the baby bottle 66 by the threads 68 to be filled with the mother's milk. Located between the bottle and the third opening of the manifold are a pair of washers 70 and 72 and a ball valve 74. These elements are adapted to be located adjacent the top of the bottle in the flow of air and milk from the cavity. Removal of the bottle 66 will allow removal of these washers and valve.

The valve has a fixed housing 76 with an enlarged circular support of an external diameter essentially equal to the external diameter of the washers for proper positioning within the third opening. A light weight plastic ball 80 is located within the housing with the housing having an opening thereabove 84 and therebelow 86. The ball is of such size with respect to the housing and its openings that it may be moved in contact with one of the openings or the other. The housing is formed of an upper housing part 88 with a surface to sealingly receive the ball and block the upper opening 84. A lower housing part 90 has fingers 92 to preclude sealing by the ball 80. These elements constitute a one way valve. The upper and lower parts 88 and 90 are separable one from the other by an annular groove and ring which snap together for ease of assembly, disassembly and cleaning.

In a normal static condition, the ball will be in association with the lower opening 86. Fingers 92 allow for fluid flow with the ball in this lower position. During operation, however, when the cylinders are reciprocated and a vacuum is formed within the cavity for milk extraction, the vacuum will pull the ball into contact with the first opening. The mating surfaces of the ball and housing will preclude the space within the bottle from being a part of the vacuum space of the horn, cavity and cylinders. By thus reducing the vacuum space, the efficiency of the pumping action is increased so that increased suction may be created for a reduced quantity of work by the mother performing the pumping action.

The manifold 14 and cylinders 42 and 46 are preferably formed of polypropylene with the housing 76 formed of polycarbonate and the washers and gasket of a nitrite rubber having a 35 to 45 Shore A durometer. All parts may thus be sterilized.

A stand 96 is preferably provided with the apparatus 10 for supporting the apparatus 10 and baby bottle 66 when no pumping is taking place. The stand 96 is symmetric about a vertical axis. It is formed with a flat lower surface 98 for placement on a table or the like. Upstanding sidewalls 102 define a recess 104 of such a size as to receive and support the lower end of a baby bottle 66 whether alone or attached to the apparatus 10.

In operation and use, a mother places the horn 24 of the apparatus 10 over her breast, preferably sufficiently tight to preclude the passage of air between the breast and the horn. Holding the apparatus 10 at the horn 24 or manifold 14 or bottle 66 in one hand, the mother would reciprocate the second cylinder 46 in a sliding action axially, up and down, with respect to the first cylinder 42. Upon moving the second cylinder away from the horn, the volume of space defined by the horn 24, cavity 12 and cylinders 42 and 46 would be increased causing a suction therein. It is this suction which extracts the milk from the mother's breast. During this action, the ball 80 is in its upper or inboard position sealing the upper aperture 84 thereby increasing the vacuum and suction force per unit of work performed by the mother while pumping. Extracted milk enters the cavity 12 and falls by gravity onto the ball 80 which is sealing the third opening 20. Upon sliding the second cylinder 46 upward from the expanded condition, the vacuum is relieved and the ball 80 falls into contact with the fingers 92 whereby the milk thereadjacent will fall into the bottle under the influence of gravity.

Continuing reciprocation of the second cylinder 46 with respect to the first cylinder 42 will create a sufficient pumping action to extract the necessary milk from the mother for latter feeding to the infant.

As can be understood, unscrewing the cap 52 from the second cylinder 46 will allow the second cylinder to be removed from the manifold, first cylinder 42 and manifold 14. Similarly, unscrewing the bottle 66 from the manifold 14 allows the bottle 66 to be provided with a lid or a nipple for the feeding of an infant at a latter time. Further, slots 34 formed in the inboard end 28 of the projection 30 allows the horn 24 to be manually compressed radially for the separation of the horn 24 from the manifold 14. With the bottle 66 removed, the washers 72 and 74 and ball valve 74 may be removed, disassembled and cleaned. The housing 76 of the valve 74 may be snapped apart to provide three elements: the ball 80 and the upper and lower housing halves 88 and 90. All of these steps allow for the convenient separation of the breast pump into its component elements for ease of cleaning.

The present disclosure includes that contained in the appended claims as well as that of the foregoing description. Although this invention has been described in its preferred form with a certain degree of particularity, it is understood that the present disclosure of the preferred form of the invention has been made by way of example only and that numerous changes in the detail of construction and combination and arrangement of parts may be resorted to without departing from the spirit and scope of the invention.

Now that the invention has been described, what is claimed is:

1. A breast pump for extracting milk from a mother's breast comprising:
   a central manifold having a cavity and a plurality of openings;
   a horn for coupling a mother's breast to be milked with the cavity of the manifold, the horn being symmetric about a first axis over the majority of its extent, the horn also having a projection rotatably positioned within one of the openings, the projection being symmetric about a second axis at an angle with respect to the first axis for varying the angular position of the horn with respect to the manifold for the convenience of the mother;
   a first fixed cylinder formed integrally with a second opening of the manifold;
   a second cylinder reciprocatingly received on the first cylinder for effecting a pumping action therebetween to create reduced pressure in the space within the horn, manifold and cylinders;
   a third opening within the manifold for coupling of the baby bottle therewith; and
   a ball valve located within the third opening whereby when the second cylinder is reciprocated with respect to the first cylinder and a vacuum created in the space within the horn, manifold and cylinders, the ball valve will seal the third opening and bottle from the space of reduced pressure and suck milk from a mother's breast in association with the horn.

2. The breast pump as set forth in claim 1 wherein the cylinders are symmetric about an axis extending at an angle from the manifold.

3. The breast pump as set forth in claim 1 further including a cap slidably received on the first cylinder and with internal threads matable with external threads on the inboard end of the second cylinder and an enlargement on the outboard end of the first cylinder to retain the cylinders in sliding relationship with each other.

4. The breast pump as set forth in claim 3 wherein the various components of the breast pump are all separable one from another.

5. Apparatus for extracting milk from a mother's breast comprising:
   a central manifold having a cavity and a plurality of openings;
   a horn for coupling a mother's breast to be miled with the cavity of the manifold, the horn being symmetric about a first axis over the majority of its extent, the horn having a projection rotatably positioned within one of the openings, the projection being symmetric about a second axis at an angle with respect to the first axis for varying the angular position of the horn with respect to the manifold for the convenience of them mother;
   a first fixed cylinder formed integrally with a second opening of the manifold;
   a second cylinder reciprocatingly received on the first cylinder for effecting a pumping action therebetween to create reduced pressure in the space within the horn, manifold and cylinders;
   a cap slidably received on the first cylinder and with internal threads matable with external threads on the inboard end of the second cylinder and an enlargement on the outboard end of the first cylinder to retain the cylinders in sliding relationship with each other;
   a third opening within the manifold;
   a baby bottle separably coupled with the third opening; and
   a ball valve located within the third opening whereby when the second cylinder is reciprocated with respect to the first cylinder and a vacuum created in the space within the horn, manifold and cylinders, the ball valve will seal the third opening and the bottle from the space of reduced pressure and suck milk from a mother's breast in association with the horn.

6. The apparatus as set forth in claim 5 and further including a stand with a flat lower face and a recess for receiving and supporting the baby bottle therein.

* * * * *